United States Patent
Yang et al.

(10) Patent No.: US 11,548,855 B2
(45) Date of Patent: Jan. 10, 2023

(54) PYRAZOLE AMIDE COMPOUND AND APPLICATION THEREOF, AND FUNGICIDE

(71) Applicant: Shandong United Pesticide Industry Co. Ltd., Taian (CN)

(72) Inventors: Guangfu Yang, Wu han (CN); Hua Li, Wu han (CN); Xiaolei Zhu, Wu han (CN)

(73) Assignee: Shandong United Pesticide Industry Co. Ltd., Taian (CN)

( * ) Notice: Subject to any disclaimer, the term of this patent is extended or adjusted under 35 U.S.C. 154(b) by 390 days.

(21) Appl. No.: 16/954,022

(22) PCT Filed: Nov. 23, 2018

(86) PCT No.: PCT/CN2018/117202
§ 371 (c)(1),
(2) Date: Jun. 15, 2020

(87) PCT Pub. No.: WO2019/114526
PCT Pub. Date: Jun. 20, 2019

(65) Prior Publication Data
US 2021/0078953 A1 Mar. 18, 2021

(30) Foreign Application Priority Data
Dec. 15, 2017 (CN) .......................... 201711349062.3

(51) Int. Cl.
*C07D 231/14* (2006.01)
*C07D 231/44* (2006.01)
*A01N 25/04* (2006.01)
*A01N 25/12* (2006.01)
*A01N 43/56* (2006.01)

(52) U.S. Cl.
CPC ........... *C07D 231/44* (2013.01); *A01N 25/04* (2013.01); *A01N 25/12* (2013.01); *A01N 43/56* (2013.01)

(58) Field of Classification Search
CPC .................................................... C07D 231/14
See application file for complete search history.

(56) References Cited

U.S. PATENT DOCUMENTS

2003/0078287 A1  4/2003  Elbe et al.
2007/0299115 A1  12/2007  Gewehr et al.

FOREIGN PATENT DOCUMENTS

| CN | 1226244 A | 8/1999 |
|---|---|---|
| CN | 101056858 A | 10/2007 |
| CN | 104557709 A | 4/2015 |
| EP | 3061750 A1 | 8/2016 |
| WO | 2006027193 A1 | 3/2006 |

OTHER PUBLICATIONS

Li, Hua, et al. "Discovery of a Fungicide Candidate Targeting Succinate Dehydrogenase via Computational Substitution Optimization." J. Agricultural and Food Chemistry. (2021), vol. 69, pp. 13227-13234. (Year: 2021).*

* cited by examiner

*Primary Examiner* — John S Kenyon
(74) *Attorney, Agent, or Firm* — Volpe Koenig

(57) ABSTRACT

The present invention relates to the field of pesticides. Disclosed are a pyrazole amide compound and an application thereof, and a fungicide. The pyrazole amide compound has a structure as represented by Formula (1). The pyrazole amide compound provided by the present invention has significant control effects on soybean rust, corn rust, wheat powdery mildew, cucumber powdery mildew, and rice sheath blight even at low concentration.

6 Claims, No Drawings

PYRAZOLE AMIDE COMPOUND AND APPLICATION THEREOF, AND FUNGICIDE

CROSS REFERENCE TO RELATED APPLICATIONS

This application is a 35 USC § 371 national stage of international application No. PCT/CN2018/117202, which was filed Nov. 23, 2018, claims priority to Chinese Application No. 201711349062.3, filed on Dec. 15, 2017, and is entitled "PYRAZOLE AMIDE COMPOUND AND APPLICATION THEREOF, AND FUNGICIDE," both of which are incorporated herein by reference as if fully set forth.

FIELD

The present disclosure relates to the technical field of pesticides, and specifically to pyrazole amide compound and an application thereof, and pesticide composition containing the pyrazole amide compound.

BACKGROUND

The fungicide targeting succinate dehydrogenase (SDH) is currently one of the most important fungicide varieties, succinate dehydrogenase inhibitor (SDHI) fungicides fulfill the purpose of preventing and treating crop diseases by inhibiting the SDH activity of the pathogenic bacteria and then causing pathogenic bacteria death.

Because of the novel action mechanism and no cross resistance with other fungicides sold on the market, SDHI fungicides have become a research hot spot of many leading pesticide companies around the world.

Among the SDHI fungicides, pyrazole-carboxamide derivatives account for the majority of all inhibitors; and because of the broad-spectrum property and high fungicidal activity in the prevention and treatment of various crop diseases in agricultural production, pyrazole amide compound is the most widely studied class of succinate dehydrogenase inhibitors.

For example, the Chinese patent documents CN1226244A and CN101056858A disclose general formula of pyrazole amide compounds used as fungicides respectively, and specifically disclose certain pyrazole amide compounds containing diphenyl ether structure in the examples.

Furthermore, CN1226244A discloses two pyrazole amide compounds 12 and 21 containing diphenyl ether structure as follows:

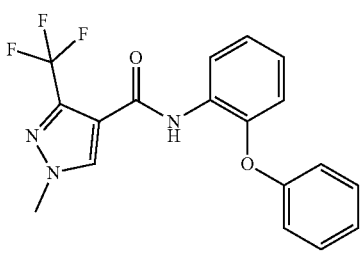

12

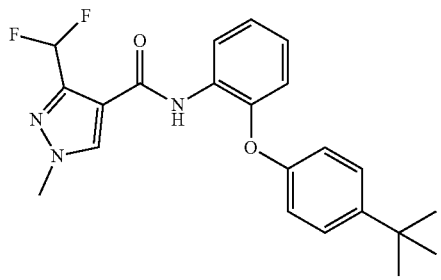

21

CN101056858A discloses the structure of pyrazole amide derivatives containing oxime-substituted diphenyl ether fragment.

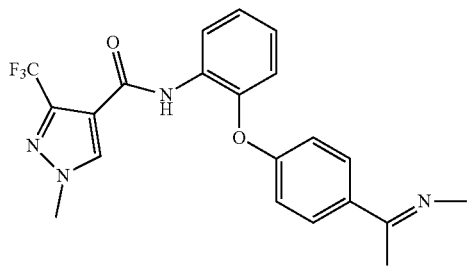 [SMILES: C/N=C(\C)c1ccc(Oc2ccccc2NC(=O)c2cn(C)nc2C(F)(F)F)cc1]

As another example, the Chinese patent document CN104557709A discloses two compounds having the following structural features.

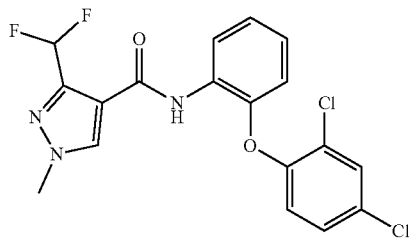

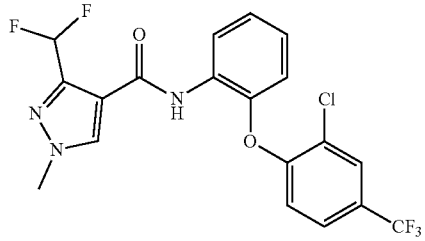

Soybean rust, corn rust, wheat powdery mildew, cucumber powdery mildew and rice sheath blight are serious crop diseases endangering agricultural production; although the commercial pyrazole amide SDHIs have fungicidal activity on one or more of the above crop diseases, the pyrazole amide SDHIs which can simultaneously prevent and treat these serious diseases at extremely low concentration have not been discovered.

For example, after biological activity tests, all compounds disclosed in CN1226244A, CN101056858A and CN104557709A have desirable fungicidal activities in the prevention and treatment of soybean rust, corn rust, wheat powdery mildew, cucumber powdery mildew or rice sheath blight at high concentration. When the concentration is reduced, the fungicidal activity of said compounds disclosed in the prior art is poor. However, the application of pesticide at high concentration may increase cost and cause significant safety issue.

SUMMARY

The present disclosure aims to overcome the defects that the pyrazole amide compounds containing diphenyl ether in the prior arts have undesirable fungicidal activities in the prevention and treatment of soybean rust, corn rust, wheat powdery mildew, cucumber powdery mildew and rice sheath blight, or exhibits poor control effects on soybean rust, corn rust, wheat powdery mildew, cucumber powdery mildew and rice sheath blight at low concentration, and provides a novel pyrazole amide compound containing diphenyl ether which has excellent control effect on soybean rust, corn rust, wheat powdery mildew, cucumber powdery mildew and rice sheath blight at low concentration.

In research, the inventors of the present disclosure discovered that the number and the position of trifluoromethyl group substitution on diphenyl ether moiety of the pyrazole amide compound have important influences on the fungicidal activities against soybean rust, corn rust, wheat powdery mildew, cucumber powdery mildew and rice sheath blight. When there are two trifluoromethyl groups on the terminal benzene ring of the diphenyl ether, and the two trifluoromethyl groups located at ortho-position and para-position respectively, coupled with no fluorine substituent at the 5-position on the pyrazole ring, the formed compound (hereinafter also referred to as "the compound of the present disclosure") can simultaneously produce desirable control effect on soybean rust, corn rust, wheat powdery mildew, cucumber powdery mildew and rice sheath blight, even at low concentration.

In particular, benzovindiflupyr is the key pesticide currently used for the control of the Asian soybean rust, however, the inventors of the present disclosure unexpectedly discovered that the control effect of the compound of the present disclosure on Asian soybean rust is comparable to that of benzovindiflupyr; moreover, the compound of the present disclosure still showed excellent control effect on wheat powdery mildew, cucumber powdery mildew and rice sheath blight at extremely low concentration, while the control benzovindiflupyr exhibited poor control effect on wheat powdery mildew, cucumber powdery mildew and rice sheath blight at low concentration. The inventors of the present disclosure completed the technical solution of the present disclosure based on the above findings.

In order to fulfill the above purpose, a first aspect of the present disclosure provides a pyrazole amide compound represented by the following Formula (1):

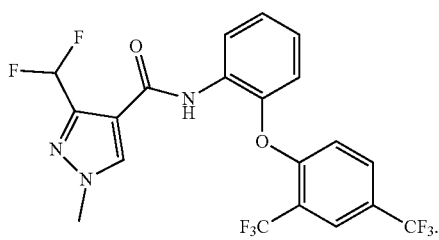

Formula (1)

A second aspect of the present disclosure provides an application of the compound according to the previously mentioned first aspect in the prevention and treatment of soybean rust.

A third aspect of the present disclosure provides an application of the compound according to the previously mentioned first aspect in the prevention and treatment of corn rust.

A fourth aspect of the present disclosure provides an application of the compound according to the previously mentioned first aspect in the prevention and treatment of wheat powdery mildew.

A fifth aspect of the present disclosure provides an application of the compound according to the previously mentioned first aspect in the prevention and treatment of cucumber powdery mildew.

A sixth aspect of the present disclosure provides an application of a compound according to the previously mentioned first aspect in the prevention and treatment of rice sheath blight disease.

A seventh aspect of the present disclosure provides an application of the compound according to the previously mentioned first aspect in the preparation of a pesticide for the prevention and treatment of at least two crop diseases selected from the group consisting of soybean rust, corn rust, wheat powdery mildew, cucumber powdery mildew and rice sheath blight.

The eighth aspect of the present disclosure provides a fungicide comprising active ingredient and auxiliary material, wherein the active ingredient comprises the pyrazole amide compound according to the first aspect of the present disclosure.

Preferably, the active ingredient is contained in an amount of 1-99.9 wt %.

Preferably, the dosage form of the fungicide is at least one selected from the group consisting of emulsifiable concentrate, suspension concentrate, water powder, dust powder, granule, aqueous solution, bait, mother liquor and mother powder.

The pyrazole amide compound with the structure shown in the formula (1) provided by the present disclosure has desirable control effect on soybean rust, corn rust and wheat powdery mildew even at low concentration.

Another important significance of the research in the present disclosure is that the field tests results proved that the compound of the present application has desirable control effect on crop diseases such as wheat powdery mildew, cucumber powdery mildew, soybean rust, corn rust and rice sheath blight. As we all known, the novel pesticide compound is initially evaluated in greenhouse pot tests, after greenhouse verification, the compound with high activity then will be enter field trails. However, because of many complicated factors such as temperature, illumination, rain, soil and so on, many compounds with high activity in greenhouse pot tests have failed to exhibit superior control effect in field trials. For example, the fungicide fenaminstrobin show extremely high activity against wheat powdery mildew in greenhouse pot test, but the control effect in field test is worse. Therefore, there are few compounds still show excellent control effect in the field trails after the greenhouse pot tests. The discovery of compounds with superior control effect infield trails often requires the technicians to pay a lot of creative labor.

Specifically, according to the field trails verification, the compound in the present disclosure exhibited the obviously superior control effects on wheat powdery mildew, cucumber powdery mildew, soybean rust, corn rust and rice sheath blight than those of corresponding commercial key pesticides, or the compound in the present disclosure exhibits considerable control effect on wheat powdery mildew, cucumber powdery mildew, soybean rust, corn rust and rice sheath blight compared with corresponding commercial pesticides.

DETAILED DESCRIPTION

The terminals and any value of the ranges disclosed herein are not limited to the precise ranges or values, such ranges or values shall be comprehended as comprising the values adjacent to the ranges or values. As for numerical ranges, the endpoint values of the various ranges, the endpoint values and the individual point value of the various ranges, and the individual point values may be combined with one another to produce one or more new numerical ranges, which should be deemed have been specifically disclosed herein.

The present disclosure does not impose specific restriction on the method for preparing the pyrazole amide compound represented by Formula (1), for example, the pyrazole amide compound represented by Formula (1) may be prepared by the following synthetic route:

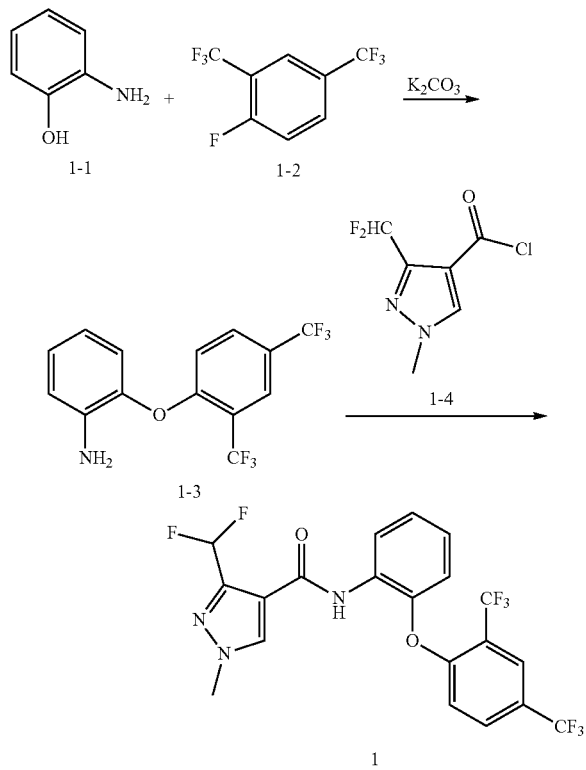

When the pyrazole amide compound represented by Formula (1) is used for preventing and treating soybean rust, corn rust, wheat powdery mildew, cucumber powdery mildew or rice sheath blight, a pesticide composition may be prepared by using a substance containing the pyrazole amide compound with the structure shown in formula (1) as an active ingredient, and used in an effective amount for the prevention and treatment of crop diseases.

The auxiliary materials in the fungicide of the present disclosure may be the adjuvants commonly used in the art for producing a variety of suitable dosage forms, including but not limited to surfactants and the other substances.

The present disclosure will be described in detail as below with reference to examples. Unless otherwise specified, each of the reagents described in the following examples is commercially available.

Each of the commercial controls in the following examples is the key pesticide currently sold on the market. For example, benzovindiflupyr is currently the commercial fungicide with highest activity against soybean rust and corn rust, prothioconazole and azoxystrobin are also staple products against soybean rust. Ethirimol, prothioconazole and fluxapyroxad are main products for preventing and treating powdery mildew on the market. Undoubtedly, the chemical structures of these commercial controls are significantly different from the compound of the present disclosure.

Example 1

The pyrazole amide compound with the structure shown in Formula (1) was prepared by using the synthetic route described in the foregoing description of the present disclosure, the specific contents were as follows:

(1) The synthesis of compound expressed by Formula 1-3

Compound expressed by Formula 1-2 (3 mmol), compound expressed by Formula 1-1 (3.3 mmol) and potassium carbonate (3.6 mmol) were added into a 50 mL round bottomed flask, dimethyl formamide (DMF, 20 mL) was further added, the mixture was stirred and heated to 100° C., when thin-layer chromatography (TLC) show the raw materials were exhausted, the reaction was stopped, then ethyl acetate (50 mL) was added, the mixture was washed with brine (50 mL*2), the organic layer was dried over anhydrous $Na_2SO_4$ and concentrated under reduced pressure, the residue was purified by column chromatography on silica gel to give the compound expressed by Formula 1-3, the yield was 55%.

Brown liquid, $^1H$ NMR (600 MHz, DMSO-$d_6$) δ 8.02 (s, 1H), 7.96 (d, J=8.5 Hz, 1H), 7.04 (dd, J=11.0, 4.3 Hz, 1H), 6.90 (dd, J=10.1, 9.0 Hz, 3H), 6.65-6.58 (m, 1H), 4.99 (s, 2H). GC-MS: M/z 321.05[M]$^+$.

(2) The synthesis of the compound expressed by Formula 1

Compound expressed by Formula 1-3 (2 mmol) was dissolved into dichloromethane (20 mL), triethylamine (3 mmol) was added, then the mixture was added dropwise with the compound represented by Formula 1-4 (in total of 2.4 mmol) under an ice bath condition. TLC showed the reaction was completed, dichloromethane (30 mL) was added, the mixture was washed with brine (50 mL*3), the organic layer was dried over anhydrous $Na_2SO_4$ and concentrated under reduced pressure, the residue was purified by column chromatography on silica gel to give the compound expressed by Formula 1, the yield was 79%.

White powder, $^1H$ NMR (600 MHz, DMSO-$d_6$) δ 9.68 (s, 1H), 8.04 (s, 1H), 8.00 (d, J=8.9 Hz, 1H), 7.96 (d, J=8.0 Hz, 1H), 7.34 (t, J=7.7 Hz, 1H), 7.29 (t, J=7.7 Hz, 1H), 7.15 (d, J=7.8 Hz, 2H), 7.09 (t, J=54 Hz, 1H), 7.07 (d, J=5.9 Hz, 1H), 3.85 (s, 3H). HRMS (MALDI) Calcd for $C_{20}H_{13}F_8N_3O_2$ [M+Na]$^+$: 502.07722, found: 502.08035.

Test Example 1: Screening Results of Fungicidal Activity in Greenhouse Pot Tests Test method: each of the test compounds in Table 1 was dispensed to 5 wt % emulsifiable concentrate (hereinafter referred to as 5% EC). The greenhouse pot test was used in each experiment, and the effective concentrations of each compound were illustrated in Table 1.

Soybean rust: two-leaf stage potted soybean seedling with uniform growth was selected and made foliar spray treatment with 5% EC, the blank control sprayed with clean water was additionally arranged, three replicates were carried out. After 24 h, the leaves of the host plants were inoculated with sporangial suspensions of the fungi soybean rust (*Phakopsora pacchyrhizi* Sydow), the plants were stored in humidity chamber (temperature 20-25° C., relative humidity>95%) and then transferred to greenhouse (25±1° C.) 8-16 h after infection. After 7 days, the screening results were investigated according to the disease incidence condition of blank control.

Corn rust: two-three leaf stage potted corn seedling with uniform growth was selected and made foliar spray treatment with 5% EC, the blank control sprayed with clean water was additionally arranged, three replicates were carried out. After 24 h, the leaves of the host plants were inoculated with sporangial suspensions of the fungi corn rust (*Puccinia sorghi*), the plants were stored in humidity chamber (temperature: lighting 25° C., dark 20° C., relative humidity 95-100%) and then transferred to greenhouse (25±1° C.) 24 h after infection. After 7 days, the screening results were investigated according to the disease incidence condition of blank control.

Wheat powdery mildew: two-leaf stage potted wheat seedling with uniform growth was selected and made foliar spray treatment with 5% EC, the blank control sprayed with clean water was additionally arranged, three replicates were carried out. After 24 h, the leaves of the host plants were inoculated by shake-down method with sporangial suspensions of the fungi wheat powdery mildew (*Erysiphe graminis*), the plants were stored in a greenhouse (25±1° C.). After 7 days, the screening results were investigated according to the disease incidence condition of blank control.

Cucumber powdery mildew: cucumber seedling in a true leaf period with uniform growth was selected, and dried in the shade for 24 h after spray treatment. Fresh cucumber powdery mildew spores on the cucumber leaves were collected and washed, and filtered through a double gauze to prepare a spores suspension with concentration of about 100,000/mL, then spray inoculation was applied. The test materials inoculated were moved into a greenhouse (lighting 21-23° C.), after 8 days, the grading investigation was carried out according to the disease incidence condition of blank control, and the control effect in a unit of % was calculated according to disease index.

The investigation method: "Guidelines for the field efficacy trials of pesticides" was adopted as the grading standard, and the control effect in a unit of % was calculated based on the disease index.

Disease index=Σ(number of diseased leaves at each grade×relative grade value)×100/(total number of leaves×9);

Control effect (%)=(disease index of control−disease index of treated)×100/disease index of control;

The test results were illustrated in Table 1.

The structures of control compounds 2-8 in Table 1 are as follows:

Compound 2

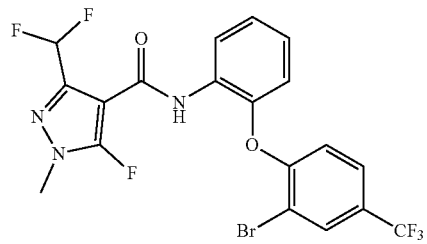

Compound 3

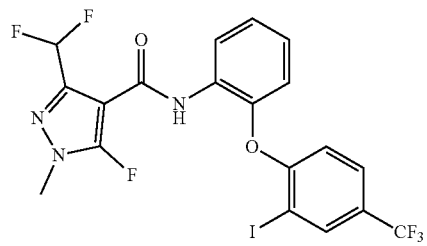

Compound 4

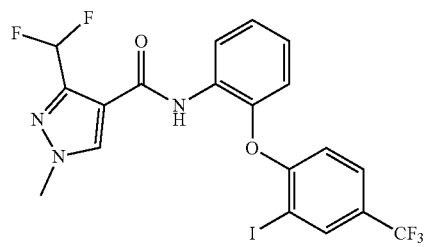

Compound 5

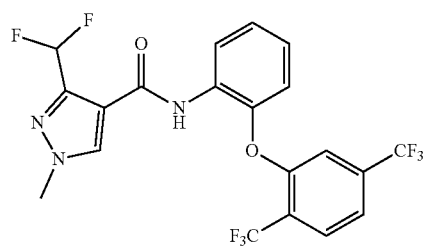

Compound 6

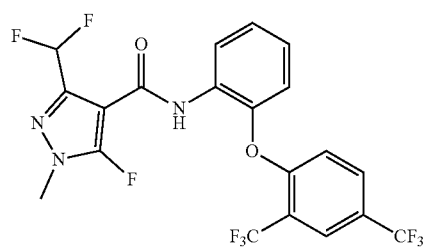

Compound 7

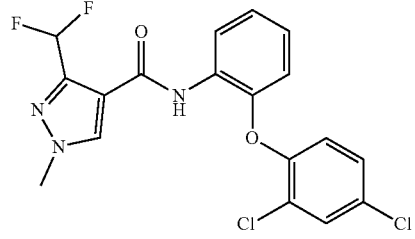

-continued

Compound 8

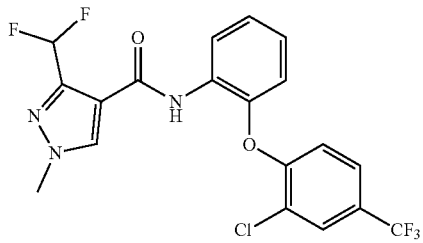

and the 5-position at the pyrazole ring of the compound 2 and compound 3 contains a fluorine substituent. According to the results from Table 1, at concentration of 25 mg/L, the control effects of the compound 2 and compound 3 on corn rust and soybean rust are equivalent to those of the compound of the present disclosure, but at concentration of 6.25 mg/L, the compound 2 and compound 3 have the defect that their control effects are poorer than those of the compounds of the present disclosure. Furthermore, the control effects of the compound 2 and compound 3 on wheat powdery mildew and cucumber powdery mildew are obviously poorer than those of the compound of the present disclosure at the same concentration. Therefore, the number of trifluoromethyl

TABLE 1

| | | Control effect (%) | | | |
|---|---|---|---|---|---|
| Number | Concentration (mg/L) | Corn rust | Soybean rust | Wheat powdery mildew | Cucumber powdery mildew |
| Compound 1 | 100 | 100 | 100 | 100 | 100 |
| | 25 | 100 | 100 | 100 | 100 |
| | 6.25 | 100 | 100 | 100 | 100 |
| Compound 2 | 100 | 100 | 100 | 85 | 88 |
| | 25 | 100 | 100 | 75 | 55 |
| | 6.25 | 98 | 96 | 70 | 45 |
| Compound 3 | 100 | 100 | 100 | 80 | 95 |
| | 25 | 100 | 100 | 80 | 70 |
| | 6.25 | 75 | 85 | 65 | 45 |
| Compound 4 | 100 | 100 | 100 | 60 | — |
| | 25 | 100 | 100 | 25 | — |
| | 6.25 | 98 | 100 | 10 | — |
| Compound 5 | 100 | 85 | 100 | 50 | — |
| | 25 | 75 | 98 | 40 | — |
| | 6.25 | 70 | 95 | 10 | — |
| Compound 6 | 100 | 100 | 100 | 92 | 98 |
| | 25 | 100 | 100 | 90 | 75 |
| | 6.25 | 98 | 90 | 85 | 50 |
| Compound 7 | 100 | 100 | 100 | 90 | 89 |
| | 25 | 95 | 98 | 75 | 60 |
| | 6.25 | 90 | 96 | 60 | 30 |
| Compound 8 | 100 | 100 | 100 | 94 | 95 |
| | 25 | 99 | 100 | 75 | 60 |
| | 6.25 | 95 | 99 | 65 | 40 |
| Benzovindiflupyr | 100 | — | — | — | 100 |
| | 25 | — | — | — | 100 |
| | 6.25 | — | — | — | 80 |
| Prothioconazole | 100 | — | — | — | 100 |
| | 25 | — | — | — | 98 |
| | 6.25 | — | — | — | 85 |
| Fluxapyroxad | 100 | — | — | — | 100 |
| | 25 | — | — | — | 100 |
| | 6.25 | — | — | — | 95 |
| Ethirimol | 100 | — | — | — | 100 |
| Difenoconazole | 100 | — | — | — | 80 |
| Azoxystrobin | 400 | — | — | — | 30 |
| | 100 | — | — | — | 0 |

As shown in Table 1, the compound provided by the present disclosure exhibited desirable control effects on corn rust, soybean rust, wheat powdery mildew, cucumber powdery mildew and rice sheath blight at low concentration. Particularly, the control effect of the compound provided by the present disclosure on wheat powdery mildew and cucumber powdery mildew at low concentration better than those of the compounds provided by the prior art.

Compared the structures of compound 2, compound 3 and compound provided by the present disclosure, we found that the ortho-position substituent on the free phenyl group of the diphenyl ether of the compound 2 and compound 3 is a halogen (the corresponding position of the compound provided by the present disclosure is trifluoromethyl group), substituent on free phenyl of diphenyl ether and the fluorine substituent at 5-position on pyrazole ring have important influence on the control effects and application range of the pyrazole amide compounds.

Compared the structural formula of the compound 4 with the compound provided by the present disclosure, the structural difference is that the ortho-position substituent on the free phenyl group of the diphenyl ether of the compound 4 is a halogen (the corresponding position of the compound provided by the present disclosure is trifluoromethyl). According to the results in Table 1, the control effects of compound 4 on corn rust and soybean rust are equivalent to those of the compound of the present disclosure at concentration of 25 mg/L or above, but the control effect of compound 4 on corn rust is poorer than that of the compound of the present disclosure at concentration of 6.25 mg/L. Furthermore, the control effect of the compound 4 at the same concentration on the wheat powdery mildew is obviously poorer than that of the compound of the present disclosure. Therefore, the number of the trifluoromethyl substituent on the free phenyl of the diphenyl ether has important influence on the control effects and the application range of the pyrazole amide compound.

Compared the structural formula of the compound 5 and the compound provided by the present disclosure, the difference is that the substituent at the 2, 5-position substituent on the free phenyl group of the diphenyl ether of the compound 5 is trifluoromethyl (the substitution position of the trifluoromethyl group of the compound provided by the present disclosure is the 2, 4-position pattern). According to the results in Table 1, the control effect of compound 5 on soybean rust is equivalent to that of the compound of the present disclosure at concentration of 100 mg/L or above, but the control effect of compound 5 on soybean rust is significantly poorer that of the compound of the present disclosure at concentration of 100 mg/L or below. Furthermore, the control effect of the compound 5 at the same concentration on wheat powdery mildew and soybean rust is obviously poorer than that of the compound of the present disclosure. Therefore, the position of the trifluoromethyl substituent on the free phenyl of the diphenyl ether and the fluorine substituent at the 5-position on the pyrazole ring have important influence on the control effects and the application range of the pyrazole amide compounds.

Compared the structural formula of the compound 6 and the compound provided by the present disclosure, the difference is that the 5-position of the pyrazole ring of the compound 6 contains a fluorine substituent (whereas the compound of the present disclosure does not have the substituent at the corresponding position). According to the results in Table 1, the control effect of compound 6 on corn rust and soybean rust is equivalent to those of the compound of the present disclosure at concentration of 25 mg/L or more, but the control effect of compound 6 on corn rust and soybean rust are inferior to that of the compound of the present disclosure at a concentration of 6.25 mg/L. Furthermore, the control effect of the compound 6 at the same concentration on wheat powdery mildew and cucumber powdery mildew are significantly lower than those of the compound of the present disclosure. Therefore, the fluorine atom at the 5-position of the pyrazole ring has important influence on the control effect and the application range of the pyrazole amide compound.

Compared the structural formula of the compound 7 and the compound provided by the present disclosure, the difference is that the substituents at the 2, 4-position on the free phenyl group of the diphenyl ether of the compound 7 are both chlorines (the substituents at the 2, 4-positions of the compound provided by the present disclosure are both trifluoromethyl groups). According to the results in Table 1, the control effect of compound 7 on corn rust and soybean rust are equivalent to those of the compound of the present disclosure at concentration of 100 mg/L or above, but the control effect of compound 7 on soybean rust is poorer that of the compound of the present disclosure below the concentration of 100 mg/L. Furthermore, the control effect of the compound 7 at the same concentration on wheat powdery mildew and cucumber powdery mildew is obviously poorer than that of the compound of the present disclosure. Therefore, the substituent pattern at the 2, 4-position of the free phenyl of the diphenyl ether has important influence on the control effect and the application range of the pyrazole amide compounds.

Compared the structural formula of the compound 8 and the compound provided by the present disclosure, the difference is that the substituent at 2-position on the free phenyl group of the diphenyl ether of the compound 8 is chlorine (the substituent at 2-position of the compound provided by the present disclosure is trifluoromethyl). According to the results in Table 1, the control effects of compound 8 on corn rust and soybean rust are equivalent to those of the compound of the present disclosure at the same concentration. However, the control effects of the compound 8 at the same concentration on wheat powdery mildew and cucumber powdery mildew are significantly lower than those of the compound of the present disclosure. Therefore, the substituent pattern at 2-position on the free phenyl of the diphenyl ether has important influence on the control effects and the application range of the pyrazole amide compounds.

Particularly, the control effect of the compound in the present disclosure on cucumber powdery mildew at low concentration (6.25 mg/L) is remarkably better that of control compounds and the existing commercial pesticide.

Test Example 2: Fungicidal Activity Screening at Low Concentration

The compounds provided by the present disclosure and some control compounds were tested by the same methods in the Test example 1, except that the effective concentrations of the compounds in this Test example are shown in Table 2.

In addition, the test method for rice sheath blight as following steps:

The potted rice seedling with uniform growth was selected, and dried in the shade for 24 h after spray treatment, then inoculated 3 blocks of 0.25 cm$^2$ rice sheath blight fungi (*Rhizoctonia solami*) at the base of seedling by clamp inoculation bacterium block method. The test materials inoculated were moved into greenhouse (temperature: lighting 28° C., dark 25° C., relative humidity 95%), after 7 days, investigate 5 leaves of per block treatment, the grading investigation was carried out according to the disease incidence condition of sheaths and leaves of rice, "Guidelines for the field efficacy trials of pesticides" was adopted as the grading standard, the disease index was calculated according to the grading standard, and the control effect in a unit of % was calculated according to disease index.

The test results of this test example are illustrated in Table 2.

TABLE 2

| Number | Concentration (mg/L) | Corn rust | Soybean rust | Wheat powdery mildew | Cucumber powdery mildew | Rice sheath blight |
|---|---|---|---|---|---|---|
| Compound 1 | 10 | 100 | 100 | 100 | 100 | 100 |
|  | 3.1250 | 100 | 100 | 100 | 100 | 100 |
|  | 2.5 | 100 | 100 | 100 | 98 | 90 |
|  | 1.5625 | 100 | 100 | 85 | 95 | 85 |
|  | 1 | — | 100 | — | 90 | 80 |
|  | 0.625 | — | — | — | — | 75 |
|  | 0.5 | — | 100 | — | — | — |
| Compound 4 | 3.1250 | 90 | 100 | 70 | — | — |
|  | 1.5625 | 50 | 98 | 30 | — | — |
| Compound 7 | 3.1250 | 60 | 100 | 50 | — | — |
|  | 1.5625 | 50 | 90 | 0 | — | — |
| Compound 8 | 3.1250 | 98 | 100 | 90 | — | — |
|  | 1.5625 | 85 | 98 | 70 | — | — |
| Benzovindiflupyr | 3.1250 | 98 | 100 | 70 | — | 65 |
|  | 1.5625 | 95 | 100 | 50 | 20 | 55 |
|  | 1 | — | 98 | — | — | 40 |
|  | 0.5 | — | 95 | — | — | 30 |
| Prothioconazole | 4 | — | 100 | 70 | 90 | — |
|  | 2 | — | 100 | 50 | 80 | — |
|  | 1 | — | 100 | 30 | 75 | — |
|  | 0.5 | — | 95 | — | — | — |
| Fluxapyroxad | 1.5625 | — | — | — | 55 | — |
| Epoxiconazole | 10 | — | — | — | — | 100 |
|  | 2.5 | — | — | — | — | 70 |
|  | 0.625 | — | — | — | — | 30 |

According to the results in Table 2, at concentration of 3.125 mg/L, the control effects of compound 4, compound 7 and compound 8 on corn rust and soybean rust are equivalent to those of the compound of the present disclosure, but compound 4, compound 7 and compound 8 have poorer control effects on corn rust and soybean rust than those of the compound of the present disclosure below the concentration of 3.125 mg/L. Furthermore, the control effects of the compound 4, the compound 7 and the compound 8 on wheat powdery mildew is significantly poorer than that of the compound of the present disclosure at the same concentration.

Moreover, according to the results in Table 2, the control effects of the compound of the present disclosure at low concentration on cucumber powdery mildew and rice sheath blight are superior to or equivalent to those of the control compounds and the existing commercial pesticide.

Test Example 3: Field Trails

I. Cucumber Powdery Mildew Test Method:

Spray method: Stein and leaf spray (Applicator: Xinkangda lithium battery electric sprayer).

Test crop: cucumber (cultivars: Tianjiao7)

The test was carried out in Shenyang, the test field was loam with rich organic matters and normal management of fertilizer and water, and no other pesticide was applied during the test.

The arrangement of the test plot was random block permutation; the area of the test plot: 15 m²; repeat times: 3 times; spray time and frequency: period between Sep. 28, 2018 and Oct. 11, 2018, twice. Spray dosage: each treatment was repeated 3 times, the total water consumption was 8 L. No other pesticide was applied during the test. The spray in the test was carried out in sunny days, and it did not rain next day. 15-20 days after the second treatment, the incidence of disease spots in each plot was investigated.

The incidence of disease spots in each plot was investigated by randomly selecting 4 samples/plot and 2 plants/samples, all leaves/plant, the incidence of the whole plant was recorded by counting the number of disease leaves and determining the incidence grade.

Grading standard (in units of leaves):

Grade 0: no leaf-spot area;

Grade 1: the ratio of leaf-spot area to leaf area is less than 5%;

Grade 3: the ratio of leaf-spot area to leaf area is between 6-10%;

Grade 5: the ratio of leaf-spot area to leaf area is between 11-20%;

Grade 7: the ratio of leaf-spot area to leaf area is between 21-40%;

Grade 9: the ratio of leaf-spot area to leaf area is more than 40%;

According to the relevant content of the "Guidelines for the field efficacy trials of pesticides of the People's Republic of China (PRC)", the disease index was calculated according to the grading standard, and the control effect in a unit of % was calculated based on the disease index, and the test data of significance analysis was performed by using DPS evaluation system (DMRT).

The results are shown in Table 3.

TABLE 3

| Number | Concentration (mg/L) | Control effect (%) Cucumber powdery mildew |
|---|---|---|
| Compound 1 | 200 | 96.5 |
|  | 100 | 90.0 |
| Pydiflumetofen | 100 | 86.0 |
| 25% Ethirimol suspension concentrate | 200 | 90.0 |

According to the results in Table 3, in terms of the control effect of field trials, the control effect on cucumber powdery mildew of the compound of the present disclosure is desirable and obviously better than mainstream pesticide pydiflumetofen and ethirimol suspension concentrate.

II. The Wheat Powdery Mildew Test Method:

Spray method: Stein and leaf spraying (Applicator: Xinkangda lithium battery electric sprayer).

Test crops: wheat (cultivars: Liaochun 10)

The test was carried out in Shenyang, the test field was loam with rich organic matters and normal management of fertilizer and water, and no other pesticide was applied during the test.

The arrangement of the test plot was random block permutation; the area of the test plot: 15 m$^2$; repeat times: 3 times; spray time and frequency: Sep. 17, 2018, once. Spray dosage: each treatment was repeated 3 times, the total water consumption was 8 L. No other pesticide was applied during the test. The spray in the test was carried out in sunny days, and it did not rain next day.

The incidence of disease spots in each plot was investigated by diagonal selecting 4 samples/plot and 20 plants/samples, and the first leaf below the flag leaf of each plant was investigated.

The grading standard of crop disease was as follows:

Grade 0: no leaf-spot area;

Grade 1: the ratio of leaf-spot area to leaf area is less than 5%;

Grade 3: the ratio of leaf-spot area to leaf area is between 6-25%;

Grade 5: the ratio of leaf-spot area to leaf area is between 26-50%;

Grade 7: the ratio of leaf-spot area to leaf area is between 51-75%;

Grade 9: the ratio of leaf-spot area to leaf area is between 76-100%;

According to the relevant content of the "Guidelines for the field efficacy trials of pesticides of the People's Republic of China (PRC)", the disease index was calculated according to the grading standard, and the control effect in a unit of % was calculated based on the disease index, and the test data of significance analysis was performed by using DPS evaluation system (DMRT).

The results are shown in Table 4.

TABLE 4

| Number | Concentration (mg/L) | Control effect (%) Wheat powdery mildew |
| --- | --- | --- |
| Compound 1 | 200 | 100 |
|  | 100 | 98 |
| Benzovindiflupyr | 100 | 95 |
| Pydiflumetofen | 100 | 91.0 |
| Prothioconazole | 100 | 93 |

The results are shown in Table 4, in terms of the control effect of field experiments, the control effect on wheat powdery mildew of the compound of the present disclosure is desirable and better than benzovindiflupyr, pydiflumetofen and prothioconazole.

III. The Soybean Rust Test Method:

Spray method: Stein and leaf spraying (Applicator: Xinkangda lithium battery electric sprayer).

Test crops: soybean (cultivars: *Glycine max*(L) Merr)

The test was carried out in Shenyang, the test field was loam with rich organic matters and normal management of fertilizer and water, and no other pesticide was applied during the test.

The arrangement of the test plot was random block permutation; the area of the test plot: 25 m$^2$; repeat times: 3 times; spray time and frequency: 2 times on Aug. 11, 2018 and Aug. 21, 2018 respectively. Spray dosage: each treatment was repeated 3 times, the total water consumption was 8 L. No other pesticide was applied during the test. The spray in the test was carried out in sunny days, and it did not rain next day. 15-20 days after the second spray treatment, the control effect was investigated.

The incidence of disease spots in each plot was investigated by diagonal selecting 5 samples/plot and 20 plants/samples, 10 leaves/plant was surveyed.

The grading standard of crop disease was as follows:

Grade 0: no leaf-spot area;

Grade 1: the ratio of leaf-spot area to leaf area is less than 5%;

Grade 3: the ratio of leaf-spot area to leaf area is between 6-25%;

Grade 5: the ratio of leaf-spot area to leaf area is between 26-50%;

Grade 7: the ratio of leaf-spot area to leaf area is between 51-75%;

Grade 9: the ratio of leaf-spot area to leaf area is between 76-100%;

According to the relevant content of the "Guidelines for the field efficacy trials of pesticides of the People's Republic of China (PRC)", the disease index was calculated according to the grading standard, and the control effect in a unit of % was calculated based on the disease index, and the test data of significance analysis was performed by using DPS evaluation system (DMRT).

The results are shown in Table 5.

TABLE 5

| Number | Dosage (mg/L) | Control effect (%) |
| --- | --- | --- |
| Compound 1 | 50 | 92.67 |
|  | 75 | 94.56 |
|  | 100 | 97.69 |
| Compound 4 | 50 | 80.14 |
|  | 75 | 85.62 |
|  | 100 | 93.11 |
| Benzovindiflupyr | 50 | 91.46 |
|  | 75 | 94.51 |
|  | 100 | 97.15 |
| Prothioconazole | 50 | 91.15 |
| FOX | 75 | 90.24 |
| Azoxystrobin | 50 | 84.62 |
| CK |  | 0.00 |

The result indicates that the compounds of the present disclosure have desirable control effect on soybean rust, its control effect is equivalent to benzovindiflupyr, and is obviously better than prothioconazole, FOX and azoxystrobin.

The above content describes in detail the preferred embodiments of the present disclosure, but the present disclosure is not limited thereto. A variety of simple modifications can be made in regard to the technical solutions of the present disclosure within the scope of the technical concept of the present disclosure, including a combination of individual technical features in any other suitable manner, such simple modifications and combinations thereof shall also be regarded as the content disclosed by the present disclosure, each of them falls into the protection scope of the present disclosure.

The invention claimed is:

1. A pyrazole amide compound having a structure represented by the following Formula (1):

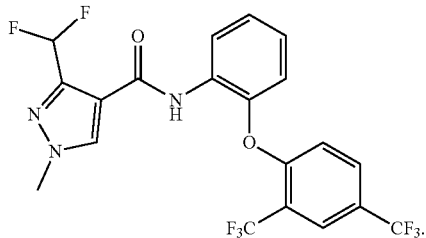

Formula (1)

2. A method of preventing or treating at least one crop disease selected from the group consisting of soybean rust, wheat powdery mildew, cucumber powdery mildew, and rice sheath blight, the method comprising applying the compound of claim 1 to a plant in need thereof.

3. A fungicide comprising an active ingredient and auxiliary material, wherein the active ingredient comprises the pyrazole amide compound of claim 1.

4. The fungicide of claim 3, wherein the active ingredient is contained in an amount of 1 wt % to 99.9 wt %.

5. The fungicide of claim 3, wherein the dosage form of the fungicide is at least one selected from the group consisting of emulsifiable concentrate, suspension concentrate, water powder, dust powder, granule, aqueous solution, bait, mother liquor and mother powder.

6. The fungicide of claim 4, wherein the dosage form of the fungicide is at least one selected from the group consisting of emulsifiable concentrate, suspension concentrate, water powder, dust powder, granule, aqueous solution, bait, mother liquor and mother powder.

* * * * *